United States Patent
Bertelli

[11] 4,055,580
[45] Oct. 25, 1977

[54] DERIVATIVES OF AMINOMETHYLCYCLOHEXANECARBOXYLIC ACID

[75] Inventor: Aldo Bertelli, Milan, Italy

[73] Assignee: Rorer Italiana S.p.A., Milan, Italy

[21] Appl. No.: 607,041

[22] Filed: Aug. 22, 1975

[51] Int. Cl.² .......................... C11C 3/00; C07F 3/00; C07C 61/01; C07C 101/00
[52] U.S. Cl. ................................ 260/404.5; 260/404; 260/448 R; 260/514 J; 260/501.11
[58] Field of Search ............... 260/404, 404.5, 448 R, 260/514 J, 501.11

[56] References Cited

U.S. PATENT DOCUMENTS

| | | | |
|---|---|---|---|
| 3,442,940 | 5/1969 | Inoue et al. | 260/514 J |
| 3,499,925 | 3/1970 | Naito et al. | 260/514 J |
| 3,839,429 | 10/1974 | Suzuki et al. | 260/514 J |
| 3,875,217 | 4/1975 | Suzuki et al. | 260/514 J |
| 3,932,497 | 1/1976 | Fukumi et al. | 260/514 J |

OTHER PUBLICATIONS

Organic Functional Group Preparations, Stanley R. Sander and Wolf Karo, 1968 Academic Press New York, pp. 274-280.
Survey of Organic Synthesis, Calvin A. Buehler and Donald E. Pearson, 1970, Wiley-Interscience New York, pp. 899-890.

Primary Examiner—Patrick P. Garvin
Assistant Examiner—William G. Wright
Attorney, Agent, or Firm—Young & Thompson

[57] ABSTRACT

The present invention is concerned with new derivatives of transaminomethylcyclohexanecarboxylic acid, which possess an anti-toxic, anti-hyperlipidic, anti-atherosclerosis, anti-phlogistic and gastroprotective activity.

The compounds of the invention are represented by the general formula:

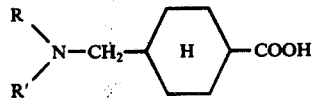

(I)

in which:
R is a group $C_nH_{2n+n'}$—CO—
n is an integer from 4 to 20,
n' is +1, −1, −3 or −5, and
R' is hydrogen or an alkyl group having 1 to 6 carbon atoms.

10 Claims, No Drawings

DERIVATIVES OF AMINOMETHYLCYCLOHEXANECARBOXYLIC ACID

The present invention is concerned with new derivatives of transaminomethylcyclohexanecarboxylic acid, which possess an anti-toxic, anti-hyperlipidic, anti-atherosclerosis, anti-phlogistic and gastroprotective activity. The invention also is concerned with a process for the preparation of these compounds and their therapeutic applications.

The compounds of the invention are represented by the general formula:

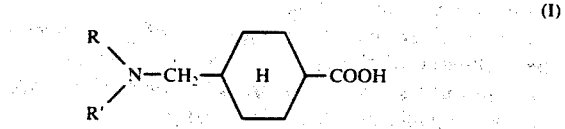
(I)

in which:

R is a group $C_nH_{2n-n'}$—CO—
n is an integer from 4 to 20,
n' is +1, −1, −3 or −5, and
R' is hydrogen or an alkyl group having 1 to 6 carbon atoms.

The invention also includes the salts of the compounds of formula (I) especially the inorganic salts of sodium, potassium, magnesium, calcium, and aluminum, and organic salts such as the salts of amino acids, for example arginine, ornithine, and lysine.

The compounds of the invention which are of particular interest are those in which R represents an oleic, linoleic, linolenic, arachidonic, decanoic, pentanoic, hexanoic, and prostanoic group.

Specific examples of compounds of formula (I) are N-oleyl-aminomethylcyclohexanecarboxylic acid, N-linoleylaminomethylcyclohexanecarboxylic acid, N-linolenyl-aminomethylcyclohexanecarboxylic acid, N-arachidoneyl-aminomethylcyclohexanecarboxylic acid, N-pentanoyl-aminomethylcyclohexanecarboxylic acid, N-hexanoyl-aminomethylcyclohexanecarboxylic acid, N-decanoyl-aminomethylcyclohexanecarboxylic acid, N-prostanoyl-aminomethylcyclohexanecarboxylic acid, derivatives of these acids with other alkyl groups substituted on the nitrogen atom, and their metal salts, in particular sodium, potassium, calcium, magnesium, aluminium, and their amino acid salts, for example, arginine, lysine, and ornithine.

The invention further provides a process for preparing the compounds of formula (I) in which an aminomethylcyclohexanecarboxylic acid of formula:

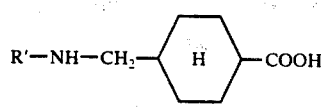
(II)

is reacted with an acid halide of formula:

R—Hal, (III)

in which R and R' have the meaning already defined and Hal is a halogen, in the presence of an acceptor for halogen acids.

As the halide, a chloride is preferably used; the acceptor of the acids may be an inorganic or organic base, in particular an amine, for example, pyridine.

The salts of the compounds of formula (I) may be obtained by conventional methods well known in the art.

The starting materials of formulae (II) and (III) are known compounds, or they can be prepared by known methods, such as those indicated in the following Examples.

The following non-limitative Examples are given to illustrate the preparation of the compounds of the invention.

EXAMPLE 1

Preparation of N-linoleyl-aminomethylcyclohexanecarboxylic acid a. Preparation of linoleyl chloride:

20 grams of linoleic acid were added to 40 cm³ of thionyl chloride. The mixture was stirred for 90 minutes. The excess thionyl chloride was distilled off under vacuum (180° to 185° C at 0.1 torr).

b. Preparation of the sodium salt of N-linoleyl-aminomethylcyclohexanecarboxylic acid:

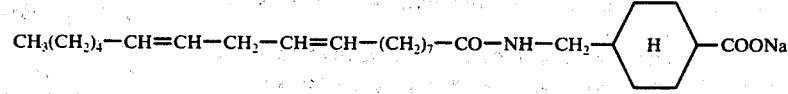

5 grams of aminomethylcyclohexanecarboxylic acid were dissolved in 50 cm³ of 6% sodium hydroxide. This solution was stirred vigorously and maintained at 10° C while 10 grams of linoleyl chloride were added drop by drop. The stirring was maintained for 1 hour at ambient temperature. The precipitate obtained on centrifuging was washed twice with acetone and allowed to dry.

The melting point was 195° to 205° C. The NMR and IR spectra, also the elementary analysis agreed with the product sought. The molecular weight was 440.6.

EXAMPLE 2

Preparation of N-decanoyl-N-aminomethylcyclohexanecarboxylic acid

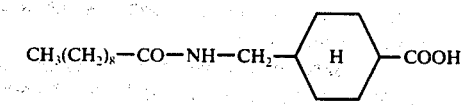

a. Preparation of decanoyl chloride:

17 grams of decanoic acid were dissolved in 40 cm³ of thionyl chloride. The mixture was allowed to stand for 1 hour, then evaporated under vacuum. The residue was dissolved in 20 cm³ of toluene and evaporated once again under vacuum. The residue was used without further purification.

b. Preparation of N-decanoyl-aminomethylcyclohexanecarboxylic acid:

3.2 grams of aminomethylcyclohexanecarboxylic acid were dissolved in 20 cm³ of anhydrous pyridine. To this solution, with stirring and without exceeding 20° C, 4 grams of decanoyl chloride were added. The solution was allowed to stand overnight, then evaporated, and the residue taken up in water. The gelatinous precipitate was filtered, washed with isopropyl ether, and then filtered again. The product was crystallized from acetonitrile. Melting point 106° C.

The compounds of the present invention show in particular an anti-cholesterolemic, anti-phlogistic and gastroprotective activity, which makes them of particular interest for therapeutic treatment.

The invention accordingly further provides a therapeutic composition which contains as its active ingredient a compound of formula (I) or a therapeutically acceptable salt thereof.

The active ingredient is generally in admixture with a therapeutically administerable vehicle or excipient.

For the purposes of illustration, the following results of a toxicological and pharmacological study on N-linoleyl-N-aminomethylcyclohexanecarboxylic acid are given; this compound being a representative example of the compounds of formula (I).

I. Toxicological Study

In tests for acute toxicity, the $LD_{50}$ of the product could not be determined in rats or mice because of its low toxicity.

It was possible to administer the product at up to 5 g/kg orally and 2 g/kg intraperitoneally, both to rats and mice, without causing death or any toxic reaction in the treated animals. The chronic toxicity of the product was equally weak.

A daily administration for 2 months, to both rats and mice, of 250 mg/kg orally or 50 mg/kg intraperitoneally, was well tolerated. Examination of the weight of the animals, their blood condition, glycemia, azotemia, and urine showed no alteration.

An anatomo-pathological and histological examination of the main organs and tissues showed no significant pathological alterations.

II. Pharmacological Study

1. Action against lipidic infiltration of the liver

Lipidic infiltration and lesions induced by carbon tetrachloride or ethanol at the hepatic level were inhibited by administration to the rat of the product at doses varying between 250 and 750 mg/kg, depending on the method of administration.

2. Anti-hyperlipidic action

Hypercholesterolemia and hyperlipemia induced in the rates by a hyperlipidic and hyperproteic diet were reduced to a normal level by daily administration of the product in doses varying between 100 and 400 mg/kg.

3. Anti-atherosclerosis action

Lesions to the arteries and heart induced in rabbits and rats by various experimental methods, (hypercholesterolemic or hyperlipemic diets and injections of adrenalin) were reduced (or their appearance prevented) by administration of the product, both orally and intraperitoneally, in doses varying between 100 and 400 mg/kg.

4. Anti-phlogistic activity

In various tests on experimental inflammation, the product showed a significant antiphlogistic action. The administration of the product in doses from 400 mg/kg or 100 mg/kg by oral and intraperitoneal routes respectively, and at a concentration of 2 to 5% for topical application, was capable of inhibiting oedema of rats paws caused by subplantar injection of carragheenin. It also inhibited generalized oedemas caused in rats by ovalbumen. Alterations to capillary permeability induced in the rat by subcutaneous injection of histamine or serotonine, were inhibited by oral, parenteral and topical administration of the product in doses respectively of 500 mg/kg, 100 mg/kg or a concentration of 2 to 5%.

5. Action on the aggregation of platelets

The aggregation of platelets induced by ADP (adenosine diphosphate) is inhibited in vitro by the product. The coagulation of platelets caused by serotonine, induced by ADP, is also inhibited in vitro.

6. Gastroprotective action

Gastric ulcers induced by ligature of the pyloris by the technique of Schay are inhibited or diminished in their seriousness by prior administration of the product intraperitoneally at 200 to 400 mg/kg.

The therapeutic composition of the present invention is suitable for human use for its anti-cholesterolemic, anti-phlogistic, anti-toxic and gastroprotective activity, in the treatment of inflammatory, toxic, hyperlipidic conditions, also in the treatment and prevention of atherosclerosis.

It may be administered orally, parenterally, rectally or topically. For these various methods of administration, it may be provided in the form of tablets, capsules, suppositories or ointments, in which the active principle is in admixture with vehicles and excipients appropriate to its pharmaceutical application.

Each unit dose may contain from 0.05 to 1 gram of active ingredient.

For the purposes of example only, the following pharmaceutical formulations of the compound of the present invention are given.

a. tablets or capsules, containing 0.25 g of active ingredient in an appropriate excipient;

b. an injectable solution containing 0.1 g of active ingredient per cm³ in an appropriate solvent;

c. suppositories, containing 0.5 g of active ingredient in a suppository base;

d. an ointment containing 10% of active ingredient in an appropriate base for this type of pharmaceutical preparation.

The doses to be administered daily vary according to the method of application envisaged.

The minimum dose is typically 1 to 2 tablets, or capsules, 2 to 3 times a day for oral administration; 1 intramuscular injection 1 or 2 times a day; rectal administration of 1 or 2 suppositories a day; topical application of an ointment 3 or 4 times a day.

Having now described my invention what I claim as new and desire to secure by Letters Patent is:

1. A compound selected from the compounds of general formula:

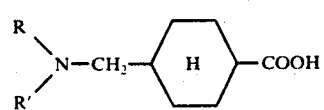

(I)

in which:

$R$ is in a group $C_nH_{2n+n'}$—CO—;

$n$ is an integer from 4 to 20, $n'$ is selected from $+1$, $-1$, $-3$ and $-5$, and $R$ is selected from hydrogen and the alkyl groups having 1 to 6 carbon atoms, and the inorganic and organic therapeutically acceptable salts thereof.

2. A compound according to claim 1, wherein said salt is selected from the sodium, potassium, magnesium, calcium, aluminium, arginine, ornithine and lysine salts.

3. N-linoleyl-N-aminomethylcyclohexanecarboxylic acid and its therapeutically acceptable salts.

4. N-decanoyl-N-aminomethylcyclohexanecarboxylic acid and its therapeutically acceptable salts.

5. N-oleyl-N-aminomethylcyclohexanecarboxylic acid and its therapeutically acceptable salts.

6. N-linolenyl-N-aminocyclohexanecarboxylic acid and its therapeutically acceptable salts.

7. N-arachidoneyl-N-aminomethylcyclohexanecarboxylic acid and its therapeutically acceptable salts.

8. N-pentanoyl-N-aminomethylcyclohexanecarboxylic acid and its therapeutically acceptable salts.

9. N-hexanoyl-N-aminomethylcyclohexanecarboxylic acid and its therapeutically acceptable salts.

10. N-prostanoyl-aminomethylcyclohexanecarboxylic acid and its therapeutically acceptable salts.

* * * * *